(12) United States Patent
Vitali et al.

(10) Patent No.: US 7,848,792 B2
(45) Date of Patent: Dec. 7, 2010

(54) DETECTION OF APNEAE AND HYPOPNEAE IN AN ACTIVE IMPLANTABLE MEDICAL DEVICE

(75) Inventors: Luca Vitali, Strambino (IT); Elodie Vincent, Antony (FR)

(73) Assignee: ELA Medical S.A.S., Montrouge (FR)

( * ) Notice: Subject to any disclaimer, the term of this patent is extended or adjusted under 35 U.S.C. 154(b) by 235 days.

(21) Appl. No.: 11/428,805

(22) Filed: Jul. 5, 2006

(65) Prior Publication Data

US 2007/0156059 A1    Jul. 5, 2007

(30) Foreign Application Priority Data

Jul. 5, 2005   (FR) ................... 05 07121
Mar. 14, 2006  (FR) ................... 06 02202

(51) Int. Cl.
*A61N 1/37*   (2006.01)

(52) U.S. Cl. ..................................... 600/509
(58) Field of Classification Search ............. 607/20; 600/509, 513, 514, 515, 527
See application file for complete search history.

(56) References Cited

U.S. PATENT DOCUMENTS

| | | | |
|---|---|---|---|
| 5,233,983 A * | 8/1993 | Markowitz | 607/42 |
| 5,304,208 A | 4/1994 | Inguaggiato | |
| 5,496,351 A | 3/1996 | Plicchi et al. | |
| 5,622,428 A | 4/1997 | Bonnet | |
| 5,722,996 A | 3/1998 | Bonnet et al. | |
| 5,766,228 A | 6/1998 | Bonnet et al. | |
| 6,015,388 A * | 1/2000 | Sackner et al. | 600/529 |
| 6,574,507 B1 | 6/2003 | Bonnet | |
| 6,830,548 B2 | 12/2004 | Bonnet et al. | |
| 7,155,278 B2 * | 12/2006 | King et al. | 607/2 |
| 7,269,459 B1 * | 9/2007 | Koh | 607/20 |
| 7,351,206 B2 * | 4/2008 | Suzuki et al. | 600/500 |
| 7,361,146 B1 * | 4/2008 | Bharmi et al. | 600/484 |
| 7,396,333 B2 * | 7/2008 | Stahmann et al. | 600/529 |
| 2004/0006375 A1 | 1/2004 | Poezevara | |
| 2004/0138718 A1 | 7/2004 | Limousin et al. | |
| 2004/0176695 A1 | 9/2004 | Poezevara | |
| 2005/0065560 A1 * | 3/2005 | Lee et al. | 607/6 |
| 2005/0131470 A1 * | 6/2005 | Vitali et al. | 607/9 |
| 2005/0137488 A1 | 6/2005 | Henry et al. | |
| 2005/0197674 A1 * | 9/2005 | McCabe et al. | 607/9 |
| 2006/0079802 A1 * | 4/2006 | Jensen et al. | 600/547 |
| 2006/0161071 A1 * | 7/2006 | Lynn et al. | 600/538 |
| 2006/0241708 A1 * | 10/2006 | Boute | 607/17 |

(Continued)

FOREIGN PATENT DOCUMENTS

EP        0515319        11/1992

(Continued)

*Primary Examiner*—Scott M Getzow
*Assistant Examiner*—Amanda Patton
(74) *Attorney, Agent, or Firm*—Orrick Herrington & Sutcliffe, LLP

(57) ABSTRACT

An active implantable medical device for diagnosis and/or therapy that is able to detect the occurrence of apnea and hypopnea. The detection of an occurrence of respiratory apneae or hypopneae is performed by collecting the patient's endocardial acceleration (EA), and determining at least one parameter, i.e., a peak acceleration, (PEA I, PEA II) that is a function of this collected endocardial acceleration. An apnea or hypopnea alert signal is then conditionally delivered as a function of the value taken by this (these) parameter(s).

30 Claims, 1 Drawing Sheet

U.S. PATENT DOCUMENTS

2007/0167851 A1 * 7/2007 Vitali et al. .................. 600/513

FOREIGN PATENT DOCUMENTS

| EP | 0655260 | 5/1995 |
| EP | 0719568 | 7/1996 |
| EP | 0750920 | 1/1997 |
| EP | 0770407 | 5/1997 |
| EP | 0970713 | 1/2000 |
| EP | 1295623 | 3/2003 |
| EP | 1336422 | 8/2003 |
| EP | 1413330 | 4/2004 |
| EP | 1433496 | 6/2004 |
| EP | 1533001 | 5/2005 |
| EP | 1537894 | 6/2005 |

* cited by examiner

DETECTION OF APNEAE AND HYPOPNEAE IN AN ACTIVE IMPLANTABLE MEDICAL DEVICE

FIELD OF THE INVENTION

The present invention relates to "active implantable medical devices" as such devices are defined by the Jun. 20, 1990 Directive 90/385/CEE of the Counsel of the European Community, and more particularly to pacemakers, defibrillators and/or cardioverter devices intended to treat heart rhythm disorders, as well as to active implantable devices that are used merely for the purpose of diagnosis. The invention is more particularly related to those devices that detect respiratory rhythm disorders occurring during a phase of sleep in a patient implanted with the device.

BACKGROUND OF THE INVENTION

In a general manner, the respiratory pathology known as "Sleep Apnea Syndrome" (SAS) is characterized by the frequent occurrence (at least 10 to 20 times per hour) of apneae during a sleep phase of the patient. An "apnea" (or respiratory pause) is defined as a temporary stop of the respiratory function, with a duration longer than 10 seconds. SAS can also be characterized by the occurrence of hypopneae under the same conditions. A "hypopnea" is defined as a significant decrease (but with no interruption) of breathing airflow, typically a decrease of more than 50% compared to an average of the preceding air flow.

Facing this pathology, that concerns more than 4% of the population, and more than 50% of the patients suffering from heart failure, the autonomic nervous system adapts, but with a noxious effect on sleep, to the interruption or reduction of breathing airflow leading to a decrease of the blood oxygen concentration, as well as unconscious micro-awakenings. That is followed, during arousal, by diurnal sleepiness with a loss of attention and increased risks of road accidents. Moreover, the physiologic, then pathologic, adaptive response of certain organs, including the heart and respiratory system, leads to a greater incidence of disorders such as arterial hypertension, ventricular arrhythmiae, myocardial infarction and heart failure.

Diverse techniques intended to detect sleep respiratory disorders by means of an implantable device are known in the prior art. For example, European patent EP 0970713 and its U.S. patent counterpart U.S. Pat. No. 6,574,507 (commonly assigned herewith to ELA Medical) discloses a device that diagnoses the occurrence of an apnea based upon a signal representing minute ventilation (VE signal, or MV signal). Minute ventilation is a parameter that is preponderantly physiological in nature, usually obtained through a measurement of a transthoracic impedance, providing a continuous indication of the patient's respiratory rhythm. This measurement of minute ventilation is performed by injecting current pulses between two electrodes positioned within the thoracic cage, or between the case of the implanted device and an electrode, for example, a pacing electrode and measuring the impedance based on the voltage as a function of the current input. The variations of impedance are correlated with the variations of thoracic volume, with peaks of impedance during inspiration, when the lungs are filled with air, and a decreasing impedance during the expiratory phase.

However, it has been observed in the field, within clinical studies, that this technique for measuring respiratory activity by recording the variations of pulmonary volume at the thoracic level may be susceptible, under certain circumstances, to the detection of false positives and false negatives that are likely to interfere with the accurate interpretation of the signals by the device.

Thus, the transthoracic impedance is varying as a function of the resistivity of the tissues at the moment when current pulse is injected; as this resistivity mainly depends on the air quantity in the lungs, and quantity of blood in heart cavities, the collected impedance signal is modulated by the respiration and heart rate. The impedance is also modulated by the variations of the distance between the measurement electrode and the device's case, a distance that is varying as a function of heart beats. Also, the respiratory component of the signal (its dynamic variation, being the only significant parameter) is added to a static component, relating to the impedance of the tissues when in stable body position, and in the absence of respiration and heart beat.

Thus, the transthoracic impedance can be modified by the patient's movements, or can vary due to the effect of diaphragmatic contractions during an obstructive apnea. These phenomena are inducing artifacts that interfere with the system, and may lead to an erroneous detection of particularly large or fast respiratory cycles, or on the contrary respiratory cycles of low amplitude and/or long period, possibly leading to false positives.

Another type of artifact may result from the presence as part of the impedance signal, of a component relating to heart beats. Indeed, under certain circumstances (for example, in situations of both bradycardia and hyperventilation), the respiratory rate and heart rate may become enough close to each other, so that the heart beats significantly influence the impedance signal. The heart rhythm may therefore be misinterpreted as a respiratory rhythm, with a risk to hide the presence of an apnea or hypopnea (false negative, at the moment when a true pathologic respiratory event occurs).

Ideally, in order to diagnose a respiratory sleep disorder, while avoiding the drawbacks of transthoracic impedance measurement, the best criterion would be a measurement of oxygen saturation in blood, the diagnosis of SAS being confirmed only in cases of confirmed and significant desaturation.

Indeed, the patients suffering from apneae or hypopneae present cyclic variations of heart rate and arterial pressure, indeed at the moment of micro-awakening and ventilatory recovery that follow the apnea, an adrenergic reaction occurs, inducing a tachycardia and an increase of heart flow that therefore compensate the hypoxemia induced by the apnea, in such a manner that, by reaction, the blood is maintained at the same level of oxygen saturation. However that direct measurement is difficult to realize in a simple and permanent way, as part of an implanted device.

OBJECTS AND SUMMARY OF THE INVENTION

The present invention, therefore, proposes an alternate approach to the diagnosis of respiratory activity disorders by an implanted device, through a detection of apneae and hypopneae that implements neither measurement of a transthoracic impedance, nor measurement of oxygen saturation in blood. Essentially, the invention proposes a detection of apneae or hypopneae based upon the measurement of endocardial acceleration, more precisely based upon the analysis of peaks of endocardial acceleration, which is a parameter reflecting in a non-artifacted way, and with a very low response time, of the variations of myocardial contractility.

So as to obtain a better detection of pathologic respiratory events, this endocardial acceleration signal can be analyzed, in the alternative, in cross-reference with some other physiologic signals such as heart rate, minute ventilation and/or patient activity, provided for instance by an acceleration sensor.

One already knows from the prior art, see, for example, European Published Patent Application EP -A-1413330 and counterpart U.S. Published Patent Application 2004/0138718 (assigned herewith to ELA Medical, and incorporated herein by reference), an implantable device comprising means for measurement of endocardial acceleration and able to diagnose and treat respiratory disorders. However, the device described by that document is analyzing ventilatory activity and is detecting the occurrence of apneae or hypopneae by analyzing the signal provided by a minute ventilation sensor based upon measurement of intrathoracic impedance. That latter device does not use endocardial acceleration for diagnosing apneae or hypopneae, but only to adapt the therapy (modulation of pacing rate) applied to the patient once the apnea or hypopnea has been detected. That device is therefore subjected to several drawbacks, as explained above, specific to the diagnosis of respiratory activity through measurement of transthoracic impedance, which requires to process the artifacted signal through the implementation of complex circuits for filtering and discrimination.

One aspect of the present invention is directed to an active implantable medical device implementing a detection of respiratory apneae and hypopneae occurring in the patient equipped with the implanted device, of the general type described in EP 09 70713 and its U.S. patent counterpart U.S. Pat. No. 6,574,507 referred to above.

In a manner characteristic of the present invention, the respiratory apneae and hypopneae are detected by collecting the patient's endocardial acceleration using a suitable means such as an accelerometer, and means for analysis, able to determine at least one functional parameter of said collected endocardial acceleration, and conditionally deliver an alert signal representative of apnea or hypopnea as a function of the value taken by said at least one parameter.

The functional parameter value is advantageously a parameter that is function of one and/or the other of two endocardial acceleration peaks over a given cycle, these two peaks comprising a first peak during ventricular isovolumetric contraction phase (PEA I), and a second peak during the ventricular isovolumetric relaxation phase (PEA II). The parameter can notably be function of (i) an average value of one or both peaks over a number of cycles, and/or (ii) a variation of the magnitude of one or both peaks over a number of cycles, and/or (iii) a difference or ratio between a long-term average and a short term average, of the value of endocardial acceleration peak(s) collected over a plurality of successive cycles. As an alternative, the parameter value can also be a function of the interval between QRS complex and at least one of the endocardial acceleration peaks, and/or of the interval between the first and second peaks of endocardial acceleration.

The means for analysis can preferably comprise means able to compare the parameter(s) to a predetermined threshold, and deliver the alert signal when this threshold is crossed.

In one preferred embodiment of the invention, the parameter value is function of a ratio between a long term average and a short term average of the values of one of the two endocardial acceleration peak(s) collected over a plurality of successive cycles, and the means for analysis comprise means for comparing this ratio to a first predetermined threshold and delivering the alert signal when the threshold is crossed.

Preferentially, the alert signal (also referred to herein as an "alarm" signal) can be delivered after crossing the first threshold only if the latter remains crossed during a predetermined minimum duration, or over a predetermined number of heart cycles.

In addition, the means for analysis can further comprise means able to, after crossing said first threshold, detect a reverse crossing of said first threshold followed by crossing a second threshold, higher than the first; and to deliver a signal of confirmation of the apnea or hypopnea episode when the second threshold is crossed. This confirmation signal is preferentially delivered only if crossing of the second signal occurs during a predetermined maximum duration, or during a predetermined maximum number of heart cycles, after reverse crossing of the first threshold.

In alternative or in addition, the means for analysis can comprise a state machine or neuronal network able to compare a plurality of parameters to a plurality of predetermined thresholds, to detect crossing of the different thresholds, analyze the sequence of crossings and to deliver said alert signal upon detection of one or more predetermined sequences of crossings.

One can also look into means for applying to endocardial acceleration: an autocorrelation function, morphologic analysis, frequential analysis and/or wavelet analysis.

Advantageously, the means for detection further comprise means for collecting the heart rate and/or respiratory activity, and/or at least one phase of exercise and/or rest of the patient. In that case, the means for analysis conditionally delivers the alert signal, as a function of one or more of the value taken by the parameter(s) and heart rate, respiratory activity signal and/or signal of the patient's status.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which.

DETAILED DESCRIPTION OF THE INVENTION

Regarding the software-related aspects thereof, the present invention can be implemented by means of an appropriate programming of the software of a known microprocessor—based active implantable device, for example, of the pacemaker, or defibrillator/cardiovertor type, comprising means for acquiring a signal provided by endocardial leads and/or one or more implanted cardiac sensors.

The invention can notably be applied to the implantable devices marketed by ELA Medical, Montrouge, France, such as the Symphony and Rhapsody brand pacemakers. These devices are equipped with programmable microprocessors and memory, including circuits intended to acquire, format and process electrical signals collected by implanted electrodes, and deliver pacing pulses to these electrodes. It is also possible to upload towards these devices, by telemetry, pieces of software that will be stored in internal memory and run so as to implement the features of the invention, described in more detail below. Implementing the features of the invention into these devices is easily within the abilities of a person of ordinary skill in the art, and will therefore not be described in detail in this document.

The prior art already teaches how to collect an endocardial acceleration signal, as it is described for instance in EP 0515319 and its U.S. patent counterpart U.S. Pat. No. 5,304, 208 (assigned to Sorin Biomedica Cardio SpA), which discloses an endocardial lead equipped with a distal pacing electrode implanted in the fundus of a cardiac cavity (left or right ventricle, or even in the atrium), integrating a microaccelerometer allowing to measure endocardial acceleration, and which disclosure is incorporated herein by reference in its entirety. The endocardial acceleration signal thus measured over one heart cycle presents, among other things, two peaks corresponding to the two major noises that can be distinguished for each beat of a healthy heart. EP 0655260 and its U.S. patent counterpart U.S. Pat. No. 5,496,351 (assigned to Sorin Biomedica Cardio SpA) describes a technique for processing endocardial acceleration signal provided by the sensor at the tip of the lead, so as to derive, notably, these two values of endocardial acceleration peaks, particularly useful for detecting heart disorders, and for triggering or not a defibrillation therapy. The disclosure of U.S. Pat. No. 5,496, 351 is incorporated herein by reference.

Figure 1:
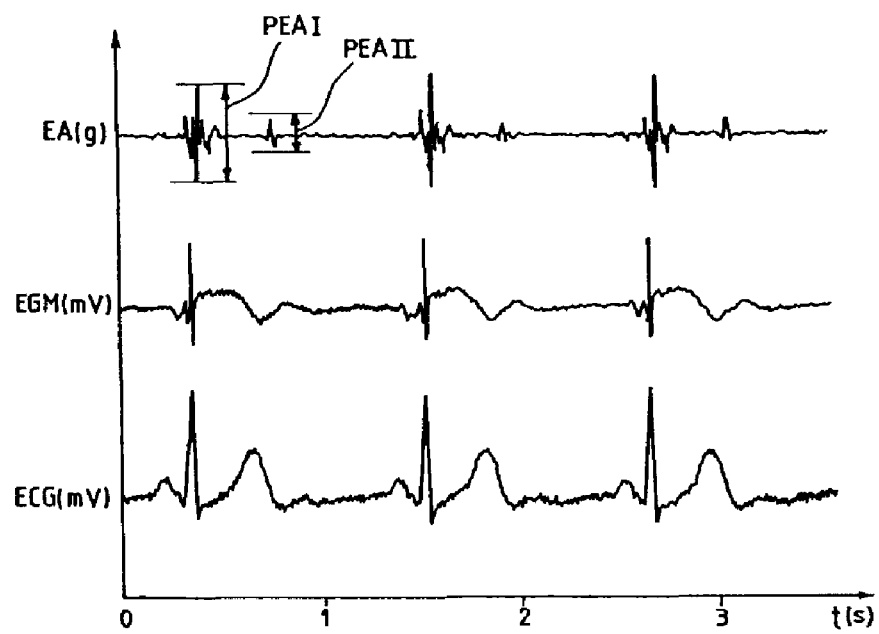
FIG. 1 is a time diagram showing the variations, over three successive heart cycles, of endocardial acceleration, and a corresponding electrogram and surface electrocardiogram.

The top curve on FIG. 1 shows the variations of endocardial acceleration (EA), measured by a sensor such as that described in EP 0515319 and U.S. Pat. No. 5,304,208 referred to above, integrated at the tip of an endocardial lead placed in the fundus of the ventricle. This figure also shows the electrogram (EGM) trace, i.e., the electrical signal collected by the distal electrode of this sensor, and the corresponding surface electrocardiogram (ECG), over three successive heart cycles. As it can be seen, the endocardial acceleration presents two successive peaks, the amplitudes of which can be determined by an appropriate processing of the signal provided by the acceleration sensor, as described in EP 0 655 260 and U.S. Pat. No. 5,496,351 referred to above. As used hereafter the term "peak" refers to the maximum peak-to-peak value of the acceleration signal separating the two extrema, positive and negative, corresponding to the variances PEA I and PEA II shown on the time diagram of FIG. 1.

More precisely, the first endocardial acceleration peak ("PEA I") corresponds to the closure of mitral and tricuspid valves, at the beginning of the phase of isovolumetric ventricular contraction (systole). The variations of this first peak are closely related to pressure variations in the ventricle (the amplitude of PEA I peak, being more precisely correlated to the positive maximum of pressure variation, dP/dt, in the left ventricle) and can therefore constitute a representative parameter for myocardium contractility, being itself correlated to the level of activity of the sympathetic system.

The second peak of endocardial acceleration ("PEA II") corresponds to the closure of aortic and pulmonary valves, during the phase of isovolumetric ventricular relaxation. That second peak, which is produced by the brutal deceleration of moving blood mass in the aorta, constitutes a representative parameter for peripheral blood pressure at the beginning of the diastole. It also constitutes a key-parameter of the physiologic process leading to the occurrence of a vasovagal syncope.

The values of PEA I and/or PEA II are collected over successive cycles, as well as heart rate, eventually.

These signals can be processed through different techniques.

A first technique concerns determining, cycle to cycle, the absolute values taken by these parameters, and to set an alarm-triggering threshold—or, preferentially, determine an averaged value of these parameters over a predetermined number of cycles, so as to avoid any influences from cycle-to-cycle variability (dispersion of measurements) and from non-significant brief events.

In order to determine the presence or absence of apnea or hypopnea, one or more thresholds are set, and each of the parameters PEA I or PEA II (or a combination of these two parameters) is compared to a predetermined threshold. The result of this comparison can be combined in different ways with the result of similar comparisons between other parameters (notably the heart rate) in order to provide an output signal with two states, one of the states being associated to a normal situation, and the other state being associated with an apnea or hypopnea alert.

In order to improve the specificity of detection, and notably to take into account the differences in basic values of PEA parameters from one patient to another, one can advantageously analyze the variations of these parameters, rather than absolute values.

One way to proceed is directed to analyzing the difference between a short term average and long term average of the same parameter. If this parameter does not vary much, the difference will be low and the two values will tend to coincide. Reciprocally, as soon as the parameter becomes unstable, the short-term average will follow the variations of the parameter more rapidly than the long-term average. Then the difference between the two averages will no longer be null or close to null, but will have a positive value (in case of increase of the parameter) or negative value (in case of decrease), the absolute value of this variance being dependent upon the analyzed parameter and the rate of change thereof.

It is also possible to follow the ratio between short-term and long-term average of PEA I and/or PEA II parameters, instead of following the difference.

Figure 2:
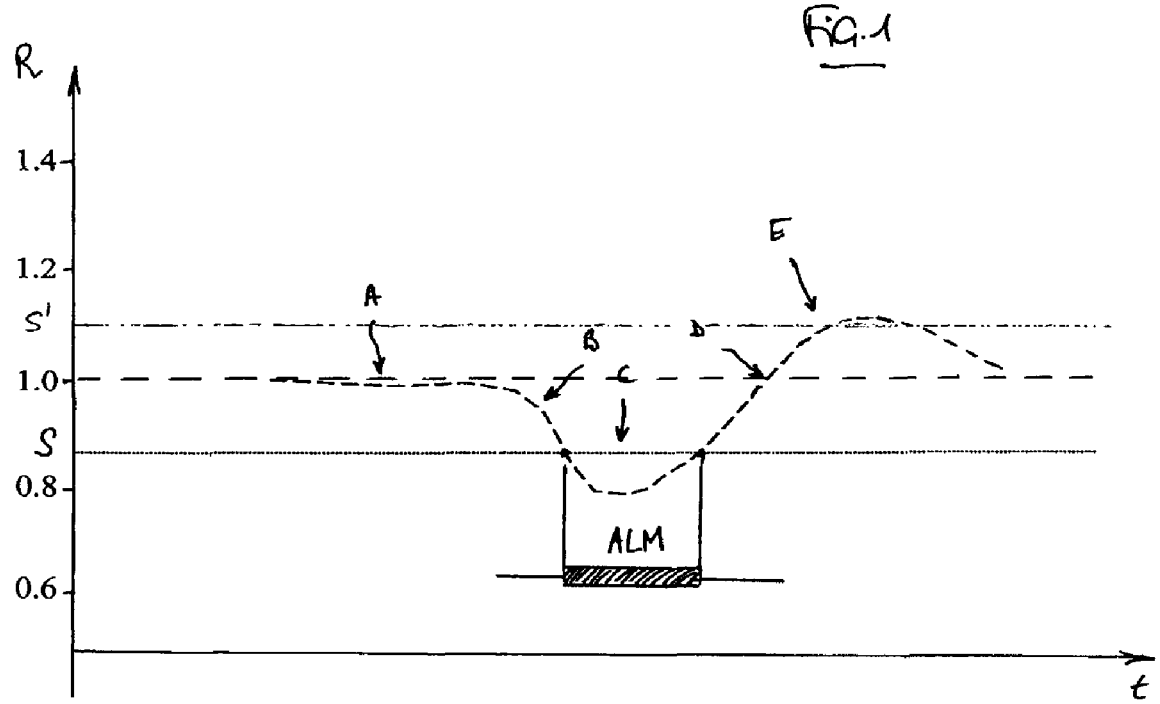
FIG. 2 shows the variations of the ratio between a short term average and a long term average of a representative peak endocardial acceleration during a typical apnea episode.

Thus, with reference to FIG. 2, an example of algorithm for apnea detection consists of calculating a short-term moving average of cycle-to-cycle values of PEA I parameter, for example, over 4 consecutive cycles. Simultaneously, a long-term moving average, for example, over 500 cycles, of this same parameter PEA I is calculated and updated. The two averages are then compared so as to provide a ratio R, with R=short-term average/long-term average. Preferably, the number of cycles as between the short term average and the long term average can differ by at least one and even more preferably about two orders of magnitude.

In the steady state or arousal condition the ratio R has an relatively constant value close to 1. On the contrary, during an apnea episode, the diminution of blood oxygen saturation induces a reduction of cardiac contractility that is translated by corresponding decrease of the amplitude of PEA I parameter over several consecutive beats, and therefore there is a correlative decrease of the value of the ratio R.

That situation is illustrated by FIG. 2, where A represents the beginning of the apnea episode and B corresponds to the moment when endocardial acceleration dramatically drops down following the reduction of contractility.

It is possible to trigger an alarm by defining a threshold S that is appropriate for ratio R, for example S=0.85 or S=0.9, and by comparing the current value of ratio R to that threshold. Each time the ratio R falls below that threshold (illustrated by C on FIG. 2), an alarm (ALM) is triggered. This alarm can be triggered immediately, at the moment the threshold is crossed, or in a conditional manner, for example, only if the ratio R remains below the threshold during a minimum predetermined duration (for example, 5 seconds), or over a predetermined minimum number of cycles (for example, 5 cycles).

Triggering of the alarm therefore indicates an episode of sudden depression of cardiac contractility, that is associated to an apnea (or hypopnea) episode. In response, it is notably possible to trigger the recording of diagnosis information in a memory of the device (marker of apnea occurrence, timestamping of this apnea, duration of the alarm, . . . etc.).

The alarm can also be used to schedule an appropriate therapy. For instance, the implanted device can increase the pacing rate so as to maintain the heart function at an appropriate level allowing a satisfactory irrigation of tissues, the latter being compromised during apnea episodes, due to the fact cardiac output is reduced due to insufficient activity of the sympathetic system.

The therapy that is scheduled by the alarm can be prolonged until the ratio R gets back to its basic level, i.e., to around R=1 (the reference D on FIG. 2 shows the end of apnea episode).

In an alternative embodiment, the therapy can be independently programmed for a fixed duration, this programmable duration being determined so as to be prolonged far beyond an isolated apneic episode, in order to ensure a support towards cardiac function during a longer period of time.

Moreover, one usually observes after the end of the apnea episode, a phenomenon of rebound, corresponding to a transitory increase of cardiac contractility (this rebound is illustrated by E on FIG. 2). More precisely, in the end of an apnea episode, a microwakening often occurs, during which the sympathetic system is activated in reaction to previous events; that reaction spontaneously ends after a certain number of heart cycles, the ratio R progressively returning to its basic value close to 1. That phenomenon of rebound can be detected and utilized so as to confirm the occurrence of the apnea episode. To that end, a second threshold S' is defined, with a value higher than 1, for example S'=1.1, and the crossing of this second threshold S' is detected after detection of an apnea episode. It shall be noted that crossing of the threshold S' simply reveals a positive reaction of sympatheticovagal system whose state is abnormal due to the apnea, that reaction being not pathologic per se, and shall not trigger the alarm nor any particular therapy.

However, the joint detection of (i) a diminution of PEA revealing a reduction of contractility, detected by crossing of the first threshold S (ratio R<0.85), followed by (ii) an increase of PEA, detected by crossing of the second threshold (ratio R>1.1), occurring (iii) within a predetermined time interval, for example, over a time interval of one minute, is a strong index of a non-physiologic state typically encountered in patients suffering from sleep disorders.

The detection of such a typical profile of PEA variation can be utilized to calculate a specific index, allowing to diagnose in the patient the presence or absence of instability of sympathetico-vagal system. This diagnosis can allow to optimize the parameters that are specific to the therapy to be applied to the patient.

For example, the detection of a recurring profile of decrease/increase of PEA can be associated to a high seriousness of the patient's disorders, leading to choose a stronger therapy, for instance a higher pacing rate and/or a faster response when a decrease of PEA is detected. Parameterization of the therapy can be operated either manually by the physician upon diagnosis, or automatically, in an adaptive manner, by the implanted device.

Reciprocally, a better stability of PEA can be associated to a less severe condition of the patient, leading to program a more moderate therapy.

Optionally, it is possible to combine this analysis of PEA with a parallel analysis of heart rate, in order to improve sensitivity and specificity of the detection and classification of apnea episodes.

In an alternate embodiment, it is possible to take into account the PEA II parameter as an alternative or addition to PEA I for the detection of apneae as described above. PEA II can be utilized as an indicator for a reduced contractility, insofar as it is correlated to the variations of blood pressure. More precisely, a reduced contractility combined with a slowing-down of heart rhythm induces a diminution of blood pressure that is translated by a reduction of PEA II amplitude. The analysis of this parameter thus allows to confirm the apnea episodes, and trigger and/or modify the specific therapy to be applied to treat these episodes of apnea or hypopnea.

Some other types of analyses, more complex, can also be implemented in order to further refine the reliability of the detection process, for instance techniques of correlation, morphology analysis of the signal, frequantial analysis, wavelet analysis, principal components analysis, etc.

It is also possible to use a "state machine" type of process in which the results of the comparisons to different thresholds are applied to a state transition system with memory management, that takes the decision to trigger an apnea or hypopnea alert as a function of a more complex evolution scheme.

The detection process can also take into account not only the parameters PEA I and/or PEA II, but also some other parameters such as heart rate, or signals provided by a minute ventilation sensor or an activity sensor. Indeed, the heart rate is decreasing at the beginning of the respiratory event and is increasing at the moment of the micro-awakening that follows the event, and presents a characteristic variability during the occurrence of the event. As to the ventilation, it presents a stop of respiratory flow over at least ten seconds and/or a reduction of at least 50% of this flow over at least ten seconds.

Finally, the diagnosis has an interest only when the patient is at rest; as these variations of respiratory activity occurring during a phase of arousal are usually non-pathologic. The simplest way of detecting sleep phases of the patient consists of using the internal clock of the device, commuting an index at given hours. It is also possible, as described in EP 0719568 and its U.S. patent counterpart U.S. Pat. No. 5,622,428 (commonly assigned herewith to ELA Medical), to operate the discrimination between sleep and arousal by analyzing the minute ventilation signal: indeed, the circadian variation of the rate and amplitude of successive respiratory cycles of the patient is well reflected by this signal and a calculation of the average ventilation over 24 hours allows to operate a satisfactory discrimination between an arousal ventilation and sleep ventilation.

It is also possible to use an activity sensor, typically an accelerometer ("G"sensor), whose signal allows to detect the patient's movements; the information provided by this type of sensor is not very specific per se to phases of arousal and sleep, but the person of ordinary skill in the art knows how to combine the signals provided by a G sensor and an MV sensor so as to deduce significant information, as it is for example described in EP 0750920 and EP 0770407 and their respective U.S. patent counterparts U.S. Pat. Nos. 5,722,996 and 5,766,228 (commonly assigned herewith to ELA Medical), to which one can refer for further details.

The device can also comprise means allowing not only to diagnose the occurrence of a Sleep Apnea Syndrome (SAS), but also to characterize more precisely certain events such as apnea, hypopnea or respiratory pause, or particular respiratory profiles, such as profiles of Cheynes-Stokes type. One can refer to EP 0970713, EP 1336422 and EP 1295623 and their respective U.S. patent counterparts U.S. Pat. No 6,574, 507, Published Patent Appl. US 2004/0006375 and U.S. Pat. No. 6,830,548 (commonly assigned herewith to ELA Medical).

One can further look into an auto-adaptive system, i.e., a system able to adapt to long term variations, in order to postrequisitely adjust the specificity of the detection system.

Also, the endocardial acceleration signals and/or values of the different PEA parameters can be stored in a device's memory, concurrently with some other signals or markers. This storage can be triggered under certain programmed conditions or upon detection of certain status (sleep) or events (occurrence of an apneic episode). The stored signals can postrequisitely be visualized by a physician equipped with a programmer able to read the device's memory contents. It can also be possible, at this point, to analyze the PEA signal in order to extract certain parameters that are not determinable in real-time, such as sinus variability, or to simulate the application of detection algorithms in order to choose the one that is the most appropriate to the patient.

Finally, the device of this invention can be utilized either for purely diagnostic purpose, or to apply an appropriate therapy in case of occurrence of detected apneae or hypopneae. Thus, following a technique already known per se, if an apnea occurs during a sleep phase of the patient, the device can, if some other criteria are fulfilled, deliver a cardiac pacing pulse at a slightly higher rate than the spontaneous sinus rate of the patient (a conventional technique known as "overdriving"), in order to increase blood flow so as to reduce the incidence of oxygen desaturation that is consecutive to SAS. These techniques are notably described in EP 0970713 and EP 1413330 and U.S. Pat. No. 6,574,507 and U.S. 2004/0138718 referred to above, to which one may refer to for further details on this technique.

One skilled in the art will appreciate that the present invention can be practiced by other than the described embodiments, which are presented for purposes of illustration and not of limitation.

We claim:

1. An active implantable medical device for detection of the occurrence of apneae and hypopneae, comprising:
   means for collecting endocardial acceleration (EA) signals from a patient implanted with the device using an endocardial lead implanted in the patient's heart over at least two heart cycles;
   means for determining from the endocardial acceleration signals the two endocardial acceleration peak values comprising a first peak value (PEA I) corresponding to the peak-to-peak value of the endocardial acceleration signals during an isovolumetric ventricular contraction phrase and a second peak value (PEA II) corresponding to the peak-to-peak value of the endocardial acceleration signal during the isovolumetric ventricular relaxation phase;
   means for calculating a long-term average of at least one of the two endocardial acceleration peak values during a first number of cycles of the at least two heart cycles and a short-term average of the at least one of the two endocardial acceleration peak values during a second number of cycles of the at least two heart cycles;
   means for determining a value as a function of the long-term average and the short-term average of the at least one of the two endocardial acceleration peak values; and
   means for conditionally delivering an output signal representative of an apnea or a hypopnea alert state of the patient based on the value.

2. The device of claim 1, wherein said value is a function of:
   (i) the variation, and/or
   (ii) a difference or a ratio, of the long term average and the short term average of the at least one of the two endocardial acceleration peak values.

3. The device of claim 2, wherein:
   said difference or ratio (R) is collected over a plurality of successive heart cycles,
   said means for determining the value further comprises means for comparing said difference or ratio to a first threshold (S), and
   said means for conditionally delivering delivers said output signal (ALM) in response to a crossing of said first threshold.

4. The device of claim 3, wherein the means for conditionally delivering delivers said output signal after crossing of said first threshold only if said first threshold remains crossed during one of a predetermined minimum duration and a predetermined minimum number of heart cycles.

5. The device of claim 3, wherein the means for determining the value further comprises means, responsive to the crossing of said first threshold, for detecting a reverse crossing of said first threshold followed by crossing of a second threshold, said second threshold being higher than the first threshold, and the means for delivering delivers a signal of confirmation of an apnea or hypopnea episode at the crossing of said second threshold.

6. The device of claim 5, wherein the means for delivering delivers said signal of confirmation of the apnea or hypopnea episode only if the crossing of said second threshold occurs during one of a predetermined maximum duration and a predetermined maximum number of heart cycles, following said reverse crossing of said first threshold.

7. The device of claim 1, wherein said value is further determined by an interval between a QRS complex and at least one of the two endocardial acceleration peak values, and/or the time interval between said first and second endocardial acceleration peak values.

8. The device of claim 1, wherein the means for determining the value further comprises means for comparing said value to a first threshold (S), wherein the means for conditionally delivering delivers said output signal (ALM) in response to a crossing of said first threshold.

9. The device of claim 1, wherein the means for determining the value further comprises a state machine or neuronal network that compares a plurality of said values to a plurality of thresholds, detects crossing of the different thresholds, analyzes the sequence of these crossings, and delivers said output signal upon detection of one or more predetermined sequence(s) of crossings.

10. The device of claim 1, wherein the means for determining the value further comprises means for applying to the two endocardial acceleration peak values, one of an autocorrelation processing, morphologic analysis, frequential analysis, and wavelet analysis.

11. The device of claim 1 further comprising means for collecting the patient's heart rate, wherein the means for conditionally delivering delivers the alert output signal as a function of both patient's heart rate and the value.

12. The device of claim 1 further comprising:
   means for collecting respiratory activity; and
   means for providing a signal of patient's ventilatory activity, wherein the means conditionally delivering delivers the output signal as a function of both the patient's ventilatory activity signal and the value.

13. The device of claim 1 further comprising;
means for detecting at least one phase of exercise and/or sleep; and
means for providing a signal of patient's status,
wherein the means conditionally delivering delivers the output signal as a function of both the patient's status signal and the value.

14. An active implantable medical device for detecting apneae and hypopneae, comprising:
means for collecting endocardial acceleration (EA) signals from a patient implanted with the device using an endocardial lead implanted in the patient's heart over at least two heart cycles;
means for determining from the endocardial acceleration signals two endocardial acceleration peak values comprising a first peak value (PEA I) corresponding to the peak-to-peak value of the endocardial acceleration signals during an isovolumetric ventricular contraction phase and a second peak value (PEA II) corresponding to the peak-to-peak value of the endocardial acceleration signal during an isovolumetric ventricular relaxation phase;
means for calculating a long-term average of at least one of the two endocardial acceleration peak values during a first number of cycles of the at least two heart cycles and a short-term average of the at least one of the two endocardial acceleration peak values during a second number of cycles of the at least two heart cycles;
means for determining at least one parameter value as a function of the long-term average and the short-term average of the at least one of the two endocardial acceleration peak values;
means for comparing said at least one parameter value to a first threshold; and
means for delivering an output signal representative of an alert state corresponding to an apnea or a hypopnea in response to said at least one parameter value crossing said first threshold.

15. The device of claim 14 wherein said at least one parameter value is averaged over a plurality of successive heart cycles.

16. The device of claim 14 wherein said long-term average and/or said short-term average are determined by a variation of said at least one parameter value over a plurality of successive heart cycles.

17. The device of claim 14 wherein said second number of cycles is less than said first number of cycles.

18. The device of claim 14 wherein said at least one parameter value is further determined by the first peak value (PEA I) measured during the isovolumetric ventricular contraction phase.

19. The device of claim 18 further comprising means for detecting a QRS complex in said patient's electrogram, wherein said at least one parameter value is further determined by an interval between a QRS complex and said endocardial acceleration peak values.

20. The device of claim 14 wherein said at least one parameter value is further determined by the second peak value (PEA II) measured during the isovolumetric ventricular relaxation phase.

21. The device of claim 20 further comprising means for detecting a QRS complex in said patient's electrogram wherein said at least one parameter value is further determined by an interval between a QRS complex and said endocardial acceleration peak values.

22. The device of claim 15 wherein said at least one parameter is further determined by a time interval between the first peak value, measured during the isovolumetric ventricular contraction phase and the second peak value measured during the isovolumetric relaxation phase.

23. The device of claim 14, wherein a difference or a ratio (R) of the long-term average and the short-term average is collected over a plurality of successive heart cycles.

24. The device of claim 15, wherein the means for delivering said output signal further comprises means for delivering said output signal in response to said first threshold remaining crossed during a predetermined minimum duration, or over a predetermined minimum number of heart cycles.

25. The device of claim 14, wherein the means for delivering said output signal further comprises means for detecting, after crossing of said first threshold, a reverse crossing of said first threshold followed by crossing of a second threshold, higher than said first threshold, and means for delivering a signal of confirmation of an apnea or hypopnea episode in response to said crossing of this second threshold.

26. The device of claim 25, wherein the means for delivering said signal of confirmation operates only if the crossing of said second threshold occurs during one of a predetermined maximum duration and a predetermined maximum number of heart cycles, following said reverse crossing of the first threshold.

27. The device of claim 14, further comprising means for collecting the patient's heart rate, wherein said means for delivering said output signal conditionally delivers said output signal as a function of both the patient's heart rate and at least one parameter value.

28. The device of claim 14 further comprising:
means for collecting respiratory activity of the patient; and
means for providing a signal of said patient's ventilatory activity,
wherein said means for delivering said output signal is as a function of both the patient's ventilatory activity signal and the at least one parameter value.

29. The device of claim 15 further comprising:
means for detecting at least one phase of exercise and/or sleep; and
means for providing a signal corresponding to the patient's status indicative of whether the patient is in a sleep phase or an exercise phase,
wherein the means for delivering said output signal conditionally delivers the output signal as a function of both the patient's status signal and the at least one parameter value.

30. The device of claim 14, wherein the at least one parameter value further comprises a plurality of parameters values, and said threshold further comprises a plurality of predetermined thresholds, said device further comprising a state machine or neuronal network for comparing said plurality of said parameters values to said plurality of predetermined thresholds, for detecting the crossing of the different thresholds, wherein said means for determining determines any sequence of these crossings and said means for delivering delivers said output signal upon detection of one or more predetermined sequence(s) of crossings.

* * * * *